United States Patent
Do et al.

(10) Patent No.: US 9,388,377 B2
(45) Date of Patent: Jul. 12, 2016

(54) REGENERATIVE CELL EXTRACTION UNIT AND REGENERATIVE CELL EXTRACTION SYSTEM

(75) Inventors: Byung-Rok Do, Seoul (KR); Jung-Kyu Lee, Seoul (KR); Ji-Hyang Kim, Seoul (KR); Sung-Guu Kang, Gyeongsangnam-do (KR); Seung-Hoon Pak, Seoul (KR); Myung-Jin Kim, Gyeonggi-do (KR); Kyu-Chul Shin, Seoul (KR); Chul-Geun Kim, Seoul (KR); Yung-Dal Yoon, Seoul (KR)

(73) Assignees: PUREBIO & TECH INC., Seoul (KR); Byung-Rok Do, Seoul (KR); Jung-Kyu Lee, Seoul (KR)

( * ) Notice: Subject to any disclaimer, the term of this patent is extended or adjusted under 35 U.S.C. 154(b) by 906 days.

(21) Appl. No.: 13/504,586

(22) PCT Filed: Oct. 25, 2010

(86) PCT No.: PCT/KR2010/007341
§ 371 (c)(1),
(2), (4) Date: Apr. 27, 2012

(87) PCT Pub. No.: WO2011/052948
PCT Pub. Date: May 5, 2011

(65) Prior Publication Data
US 2012/0214659 A1    Aug. 23, 2012

(30) Foreign Application Priority Data

Oct. 27, 2009    (KR) .......................... 10-2009-0102085

(51) Int. Cl.
*B04B 5/04*    (2006.01)
*C12M 1/00*    (2006.01)

(52) U.S. Cl.
CPC .............. *C12M 47/04* (2013.01); *B04B 5/0442* (2013.01); *C12M 45/05* (2013.01)

(58) Field of Classification Search
CPC ..... C12M 45/04; C12M 45/05; B04B 5/0442; B04B 5/0464
See application file for complete search history.

(56) References Cited

U.S. PATENT DOCUMENTS

2006/0223176 A1*    10/2006    Mandrusov et al. .......... 435/325
2008/0014181 A1*    1/2008    Ariff et al. ................. 435/308.1

FOREIGN PATENT DOCUMENTS

| JP | 9-276396 A | 10/1997 |
|---|---|---|
| JP | 2001-017540 A | 1/2001 |
| JP | 2006-020756 A | 1/2006 |
| JP | 2007-236665 A | 9/2007 |

OTHER PUBLICATIONS

International Search Report: mailed Jul. 26, 2011; PCT/KR2010/007341.

* cited by examiner

*Primary Examiner* — Timothy Cleveland
(74) *Attorney, Agent, or Firm* — Ladas & Parry LLP

(57) ABSTRACT

Provided is a regenerative cell extraction system. The regenerative cell extraction system includes: a regenerative cell separation unit which separates fat tissue; and a regenerative cell extraction unit. The regenerative cell separation unit includes: a sub container which is rotated by a torque applied from an external source and includes a space in which fat tissue is housed; a hollow main pipe which is inserted into the sub container; and a pump which is connected to the main pipe. In addition, the regenerative cell extraction unit receives a regenerative cell-containing substance, which is obtained after the fat tissue is centrifuged by the regenerative cell separation unit, from the regenerative cell separation unit, and extracts regenerative cells from the substance by centrifuging the substance. The regenerative cell extraction unit includes: a main container which is rotated by a torque applied from an external source; a hollow first discharge pipe which is inserted into the main container; and a suction device which is connected to the first discharge pipe; and a plurality of protruding housing portions which bulge outwards along a radius direction with respect to a center of rotation of the main container to accommodate relatively heavy components among components separated from the substance.

23 Claims, 10 Drawing Sheets

REGENERATIVE CELL EXTRACTION UNIT AND REGENERATIVE CELL EXTRACTION SYSTEM

CROSS-REFERENCE TO RELATED APPLICATION

This application claims the benefit under 35 U.S.C. §119 (a) of a Korean Patent Application No. 10-2009-0102085, filed on Oct. 27, 2009, the entire disclosure of which is incorporated herein by reference for all purposes.

BACKGROUND

1. Field

The following description relates to a regenerative cell extraction unit and system, and more particularly, to a system for extracting regenerative cells such as fat-derived stem cells by centrifuging fat tissue and an extraction unit used in the system.

2. Description of the Related Art

Stem cells are defined as cells that have clonogenic and self-renewing capabilities and that differentiate into multiple cell lineages. Whereas embryonic stem cells are derived from mammalian embryos in the blastocyst stage and have the ability to generate any terminally differentiated cell in the body, adult stem cells are part of tissue-specific cells of the postnatal organism into which they are committed to differentiate.

Adult stem cells offer practical advantages over embryonic stem cells. Unlike the latter, they do not raise any ethical issue, and can be extracted from the patient himself. They are in abundant supply and are intrinsic to various tissues of the human body. The most accessible sources of adult stem cells are the bone marrow, peripheral blood, umbilical cord blood and possibly adipose tissues, as indicated by recent studies. These cells are capable of maintaining, generating and replacing terminally differentiated cells within their own specific tissue as a consequence of physiologic cell turnover or tissue damage due to injury.

Such capability, known as cell plasticity, has led to the development of therapeutic applications targeting the regeneration of defected tissues, with the goal to restore the physiology and functionality of the affected organ. Adult stem cells can give rise to hematopoiteic cells as known since many decades, but as found in recent years can also give rise to blood vessels, muscles, bone, cartilage, skin, neurons etc. Such cells are known as mesenchymal stem cells. In addition, platelets prepared as platelets concentrate can be used to accelerate wound healing, and consequently can play a role in regenerative medicine to help in the reconstruction of tissues like bone, skin or other tissues.

Fat tissue has recently been found to contain large amounts of stem cells, progenitor cells and matrix suitable for therapeutic applications. Also, fat tissue is a rich source of endothelial cells that promote the growth of new blood vessels and stimulate the growth of stem and progenitor cells, thereby contributing to tissue regeneration.

While many devices have been developed to collect cells from fat tissue, they are not efficient in extracting fat tissue or are not fully automated—that is, of all processes from collecting fat tissue to processing the fat tissue, some processes should be performed manually. In addition, since these devices are not sealed completely, fat tissue is exposed to a risk of contamination while being collected and processed.

Accordingly, there is a need for the development of a device which can automatically perform all processes from collecting fat tissue to processing the fat tissue in a sealed state and can increase the purity of regenerative cells extracted from the fat tissue.

SUMMARY

The following description relates to a regenerative cell extraction unit and system which automatically perform all processes from collecting fat tissue to extracting stem cells from the fat tissue in a sealed state and are structured to extract the stem cells with increased efficiency.

In one general aspect, there is provided a regenerative cell extraction unit including: a main container which is rotated by a torque applied from an external source and includes a housing portion accommodating a substance that is to be separated; a hollow first discharge pipe which is inserted into the main container such that an end portion of the first discharge pipe is disposed in a lower part of the main container and that the other end portion of the first discharge pipe is disposed outside the main container; and a suction device which is connected to the first discharge pipe so as to suck and discharge components, which are placed in a lower end portion of the main container after being centrifuged by the rotation of the main container, from the main container through the first discharge pipe; and a plurality of protruding housing portions which bulge outwards along a radius direction with respect to a center of rotation of the main container to accommodate relatively heavy components among components separated from the substance and are arranged at intervals of a predetermined angle along a circumferential direction of the protruding housing portions.

According to the present invention, a lower part of the housing portion narrows toward a lower end of the housing portion, and a concave groove is formed in the lower end of the housing portion.

According to the present invention, the regenerative cell extraction unit further includes: a collection member which is disposed in the housing portion of the main container and includes a concave collector portion; a plurality of guide members which are formed on the collection member, are positioned to interfere with components which are rotated and pressed toward an inner surface of a wall of the main container, and guide the rotating components to the collector portion of the collection member; a hollow second discharge pipe which is inserted into the main container, has an end portion disposed above the collector portion of the collection member, and has the other end portion disposed outside the main container; and a second pump which is connected to the second discharge pipe, provides a suction force to the second discharge pipe, and discharges the components collected on the collection member to the outside through the second discharge pipe.

According to the present invention, the second discharge pipe is fitted into a through hole formed in an upper part of the main container, and the regenerative cell extraction unit further includes a medium member which enables the main container to rotate relative to the second discharge pipe while sealing a gap between an outer circumferential surface of the second discharge pipe and an inner circumferential surface of the through hole.

According to the present invention, a ring-shaped flange is formed along the outer circumferential surface of the second discharge pipe, the medium member is ring-shaped, is made of a rubber material which is compressible and elastic, and is compressed between a lower surface of the flange and an upper surface of the main container in a state where the second discharge pipe is inserted into the main container, and a ring-shaped contact member having a lower coefficient of friction than rubber is formed on an upper surface of the medium member and is attached closely to the flange, wherein while being compressed between the main container and the flange, the medium member and the contact member rotate in accordance with the rotation of the main container and seal the gap between the inner circumferential surface of the through hole formed in the upper part of the main and the outer circumferential surface of the second discharge pipe.

In another aspect, there is provided a regenerative cell extraction system including: a regenerative cell separation unit which separates fat tissue; and a regenerative cell extraction unit including the above-described elements, wherein the regenerative cell separation unit includes: a sub container which is rotated by a torque applied from an external source and includes a space in which tissue is housed; a hollow main pipe which is inserted into the sub container such that an end portion of the main pipe is disposed in a lower part of the sub container; and a pump which is connected to the main pipe and provides a suction force to the main pipe, and wherein the regenerative cell extraction unit is separate from the regenerative cell separation unit, receives a regenerative cell-containing substance, which is obtained after the fat tissue is centrifuged by the regenerative cell separation unit, from the regenerative cell separation unit through the main pipe, and extracts regenerative cells from the substance by centrifuging the substance.

Other features and aspects will be apparent from the following detailed description, the drawings, and the claims.

Figure 1:
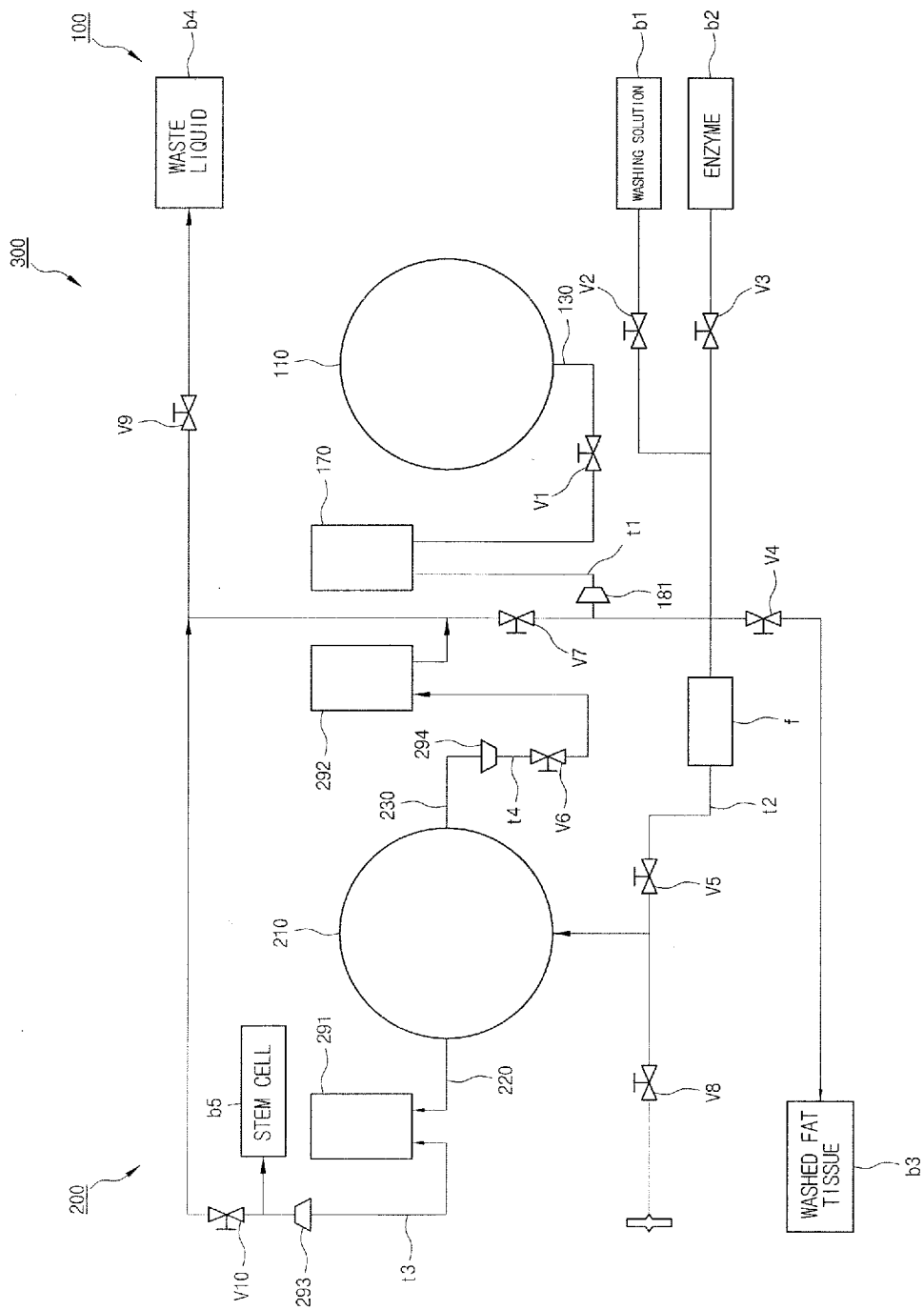
FIG. 1 is a schematic diagram illustrating the configuration of a regenerative cell extraction system according to an exemplary embodiment of the present invention.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Hereinafter, a regenerative cell extraction system and unit according to an exemplary embodiment of the present invention will be described in greater detail with reference to the accompanying drawings.

Figure 2:
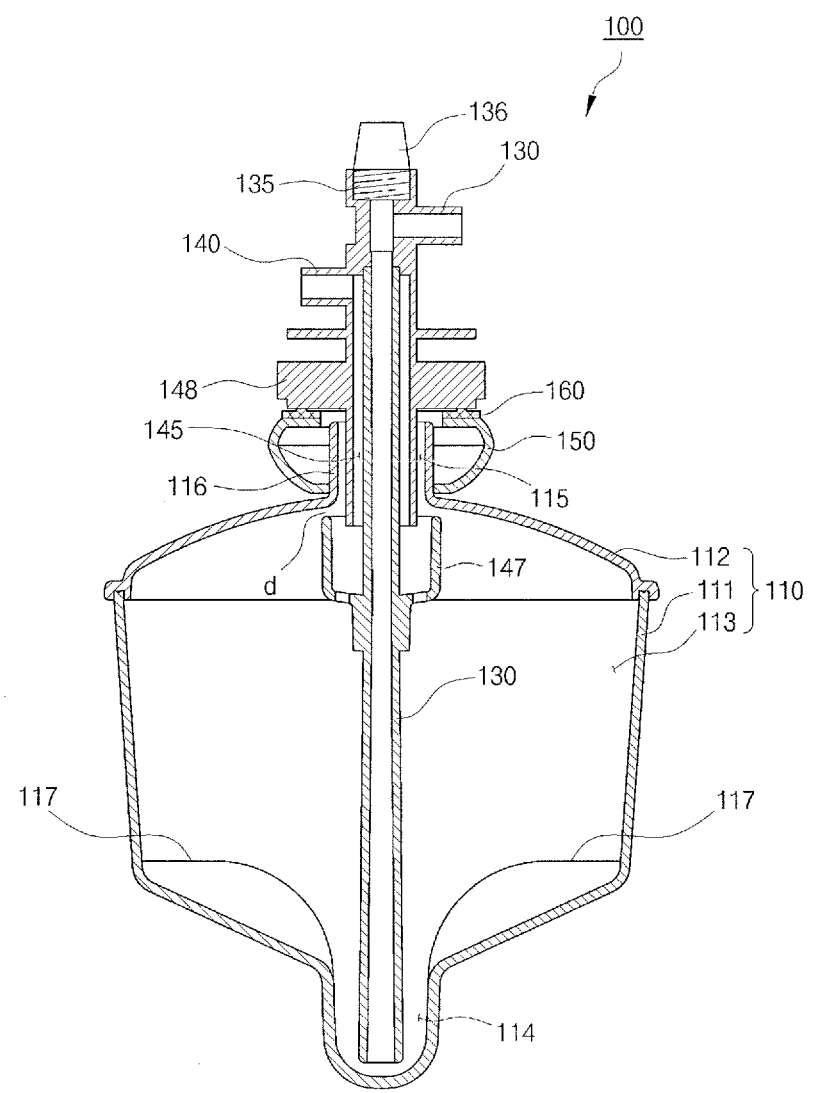
FIG. 2 is a schematic cross-sectional view of a regenerative cell separation unit shown in FIG. 1.

FIG. 1 is a schematic diagram illustrating the configuration of a regenerative cell extraction system 300 according to an exemplary embodiment of the present invention. FIG. 2 is a schematic cross-sectional view of a regenerative cell separation unit 100 shown in FIG. 1.

Referring to FIGS. 1 and 2, the regenerative cell extraction system 300 according to the current exemplary embodiment includes the regenerative cell separation unit 100 and a regenerative cell extraction unit 200. The regenerative cell separation unit 100 and the regenerative cell extraction unit 200 are connected to each other by pumps and tubes. In addition, the regenerative cell separation unit 100 and the regenerative cell extraction unit 200 are fitted to a rotating jig (not shown). Thus, while being rotated at a preset speed by the rotating jig (not shown), the regenerative cell separation unit 100 and the regenerative cell extraction unit 200 perform centrifugation.

The configuration of the regenerative cell separation unit 100 will now be described in further detail.

To centrifuge fat tissue, the regenerative cell separation unit 100 includes a sub container 110, a main pipe 130, and a pump 170.

The sub container 110 is used for centrifugation of fat tissue, and a space 113 in which fat tissue can be housed is formed inside the sub container 110. The sub container 110 includes a sub container bowl 111 and a sub container cap 112 coupled onto the sub container bowl 111.

The body of the sub container bowl 111 is gradually and slightly reduced in diameter toward a lower part thereof. Here, the diameter of the body of the sub container bowl 111 may also remain unchanged. However, the lower part of the body of the sub container bowl 111 is noticeably reduced in diameter toward a bottommost part of the body of the sub container bowl 111, and a concave groove 114 is formed in the bottommost part of the sub container bowl 111.

A through hole 115 is formed in a center of the sub container cap 112, and a protruding wall 116 extends upward from an outer circumference of the through hole 115.

Stirring wings 117 are formed in a lower part of the sub container bowl 111 and on an inner surface of a wall of the sub container bowl 111. The stirring wings 117 protrude from the inner surface of the wall of the sub container bowl 111 toward the space 113. Four stirring wings 117 are arranged symmetrical to each other at intervals of 90 degrees with respect to a center of rotation of the sub container 110. The number of the stirring wings 117 can be only one and may not necessarily be symmetrical to each other. The stirring wings 117 rotate in accordance with the rotation of the sub container 110 thereby to stir fat tissue smoothly.

The main pipe 130 functions as a fluid passage through which a washing solution, enzymes, and the like are transferred to the space 113 of the sub container 110 and substances within the sub container 110 are discharged to the outside. The hollow main pipe 130 is inserted into the sub container 110 through the through hole 115 of the sub container 110. A lower end portion of the main pipe 130 is disposed in the groove 114 of the sub container 10 to be close to a bottom of the sub container 110, and an upper end portion of the main pipe 130 is disposed above the sub container 110.

In the current exemplary embodiment, an auxiliary pipe 140 is installed. The auxiliary pipe 140 is a passage independent of the main pipe 130 and connects the inside and outside of the sub container 110. The auxiliary pipe 140 functions as a passage through which air flows into or out of the sub container 110. Therefore, there is no need to insert the auxiliary pipe 140 up to a lower end portion of the sub container 110. That is, the auxiliary pipe 140 may be inserted only up to an upper end portion of the sub container 110.

The main pipe 130 and the auxiliary pipe 140 can be formed as separate pipes. In the current exemplary embodiment, however, the main pipe 130 and the auxiliary pipe 140 are integrated. That is, the main pipe 130 is long, extends vertically, and has a bent upper part. The auxiliary pipe 140 has a greater diameter than the main pipe 130 and surrounds the main pipe 130. An upper part of the auxiliary pipe 140 is bent in a direction opposite to the direction in which the main pipe 130 is bent. The inside of the auxiliary pipe 140, more accurately, the space between an inner circumferential surface of the auxiliary pipe 140 and an outer circumferential surface of the main pipe 130 forms a fluid passage 145 through which air can flow. However, the fluid passage 145 is not necessarily used as an air passage. When necessary, the fluid passage 145 may be used as a passage through which various substances can be injected or discharged. For example, the fluid passage 145 may be used to discharge substances such as contaminants derived from blood or inject substances such as a washing solution.

An insertion hole 135 is formed in an upper end of the main pipe 130, and a cap 136 is coupled to the insertion hole 135 by screws. When the cap 136 is removed, a syringe needle (not shown) is inserted into the main pipe 130 through the insertion hole 135 to suck liquid substances placed in the groove 114 of the sub container 110. When the syringe needle is not in use, the insertion hole 135 is closed with the cap 136 to prevent the contamination of the space 113 inside the sub container 110.

A shielding member 147 is fitted to the main pipe 130 under the auxiliary pipe 140. When the sub container 110 rotates to centrifuge fat tissue, liquid substances such as blood and a washing solution may rapidly rise toward a top of the sub container 110 to be introduced into the auxiliary pipe 140 or into the auxiliary pipe 140 and the through hole 115 of the sub container 110. However, since the shielding member 147 surrounds the through hole 115 and the auxiliary pipe 140, it can prevent, e.g., blood-derived contaminants from entering the auxiliary pipe 140, for example. The shielding member 147 surrounding the through hole 115 and the auxiliary pipe 140 does not completely seal them. Instead, a gap d is formed to allow the auxiliary pipe 140 to be connected to the space 113.

Spiral auxiliary stirring wings (not shown) are formed on an outer circumferential surface of the main pipe 130. Together with the stirring wings 117 disposed in the lower part of the sub container 110, the auxiliary stirring wings stir fat tissue.

The sub container 110 should be rotated relative to the main pipe 130 and the auxiliary pipe 140, and the space 113 of the sub container 110 should be sealed by closing a gap between the main and auxiliary pipes 130 and 140 and the sub container 110.

In the current exemplary embodiment, a compressible sealing member 150 and a frictional member 160 are employed to facilitate the rotation of the sub container 110 and seal the space 113 of the sub container 110. That is, the sealing member 150 employed in the current exemplary embodiment is ring-shaped, is fitted to the protruding wall 116 of the sub container cap 112, and is interposed between a flange 148, which is formed on an outer circumferential surface of the auxiliary pipe 140, and the sub container cap 112. The sealing member 150 is made of a rubber material that can be elastically compressed. When compressed between the flange 148 of the auxiliary pipe 140 and the sub container cap 112, the sealing member 150 can completely seal a gap between the protruding wall 116 and the auxiliary pipe 140. Of course, the sealing member 150 can completely seal a gap between the through hole 115 and the auxiliary pipe 140.

However, when the sealing member 150 rotates in accordance with the rotation of the sub container 110, friction is created between the sealing member 150 and the flange 148 because the sealing member 150 made of a rubber material has a high coefficient of friction. The friction between the sealing member 150 and the flange 148 impedes smooth rotation of the sealing member 150 and produces high frictional heat. For this reason, the frictional member 160 made of a material with a low coefficient of friction and a high coefficient of heat transfer is attached onto the sealing member 150. In the current exemplary embodiment, the frictional member 160, which is made of a ceramic material and is ring-shaped, is attached onto the sealing member 150. The frictional member 160 is closely attached to the flange 148 of the auxiliary pipe 140 and makes a surface contact with the flange 148.

In other embodiments, the rotation of the sub container 110 relative to the auxiliary pipe 140 and the sealing of the gap between the sub container 110 and the auxiliary pipe 140 may be accomplished using a retainer ring (not shown) and a bearing (not shown).

In the current exemplary embodiment, the main pipe 130 and the auxiliary pipe 140 are integrated such that the auxiliary pipe 140 surrounds the main pipe 130. This structure brings about the need to seal a gap between the outer circumferential surface of the auxiliary pipe 140 and the protruding wall 116 and between the auxiliary pipe 140 and the through hole 115. In other embodiments, however, the auxiliary pipe 140 may be separate from the main pipe 130 or may be omitted. In these embodiments, the main pipe 130 is also inserted into the through hole 115. Thus, to facilitate the rotation of the sub container 110 relative to the main pipe 130 and close the gap between the main pipe 130 and the protruding wall 116 and between the auxiliary pipe 140 and the through hole 115, a flange (not shown) is formed on the outer circumferential surface of the main pipe 130, and the sealing member 150 and the frictional member 160 are installed between the sub container cap 112 and the flange (not shown) formed on the outer circumferential surface of the main pipe 130.

The pump 170 is connected to the main pipe 130 by a connection tube and provides substances such as enzymes and a washing solution to the sub container 110 through the main pipe 130 or discharges fat cells or liquid wastes from the sub container 110 to the outside. Accordingly, since a suction force should be provided in both directions, a peristaltic pump that provides a suction force while rotating in a direction or in a reverse direction is used as the pump 170 in the current exemplary embodiment.

Until now, the configuration of the regenerative cell separation unit 100 has been described. Hereinafter, the regenerative cell extraction unit 200 according to the present invention will be described in greater detail with the accompanying drawings.

Figure 3:
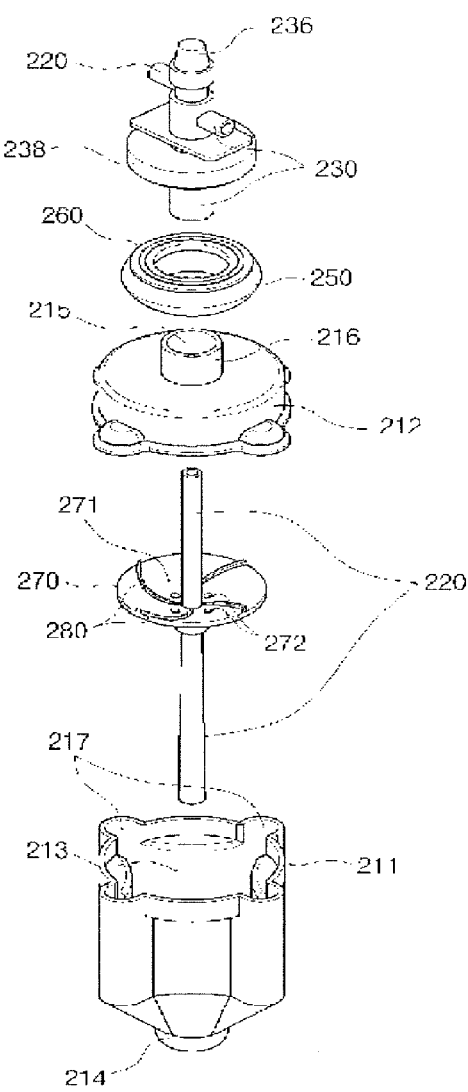
FIG. 3 is a schematic, exploded perspective view of a regenerative cell extraction unit according to an exemplary embodiment of the present invention shown in FIG. 1.
Figure 4:
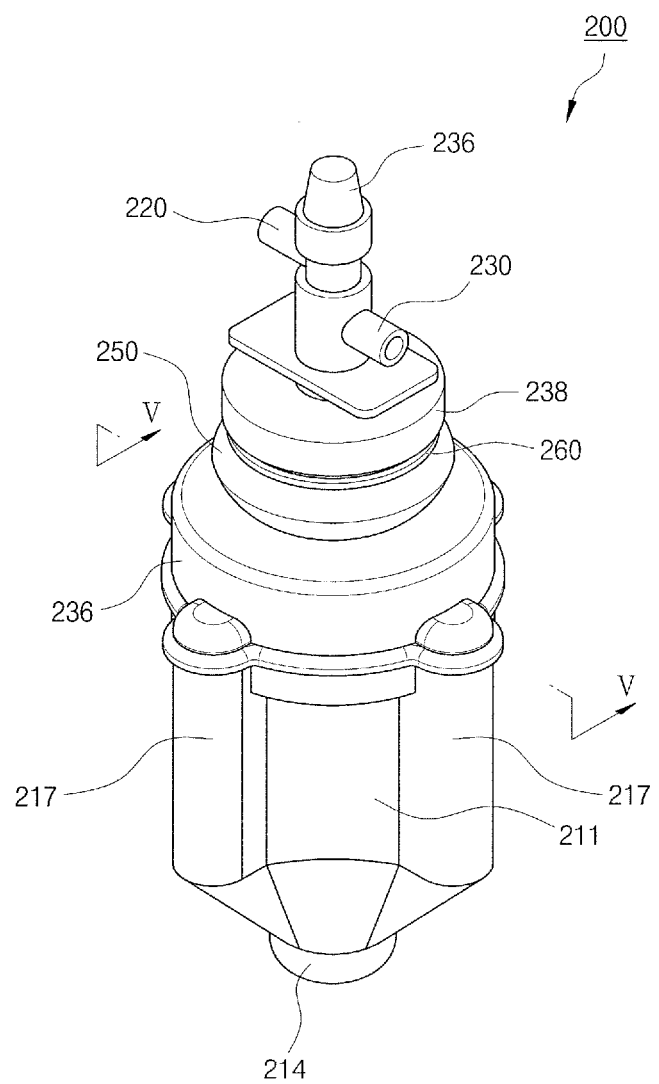
FIG. 4 is a schematic perspective view of the regenerative cell extraction unit of FIG. 3 which has been assembled.
Figure 5:
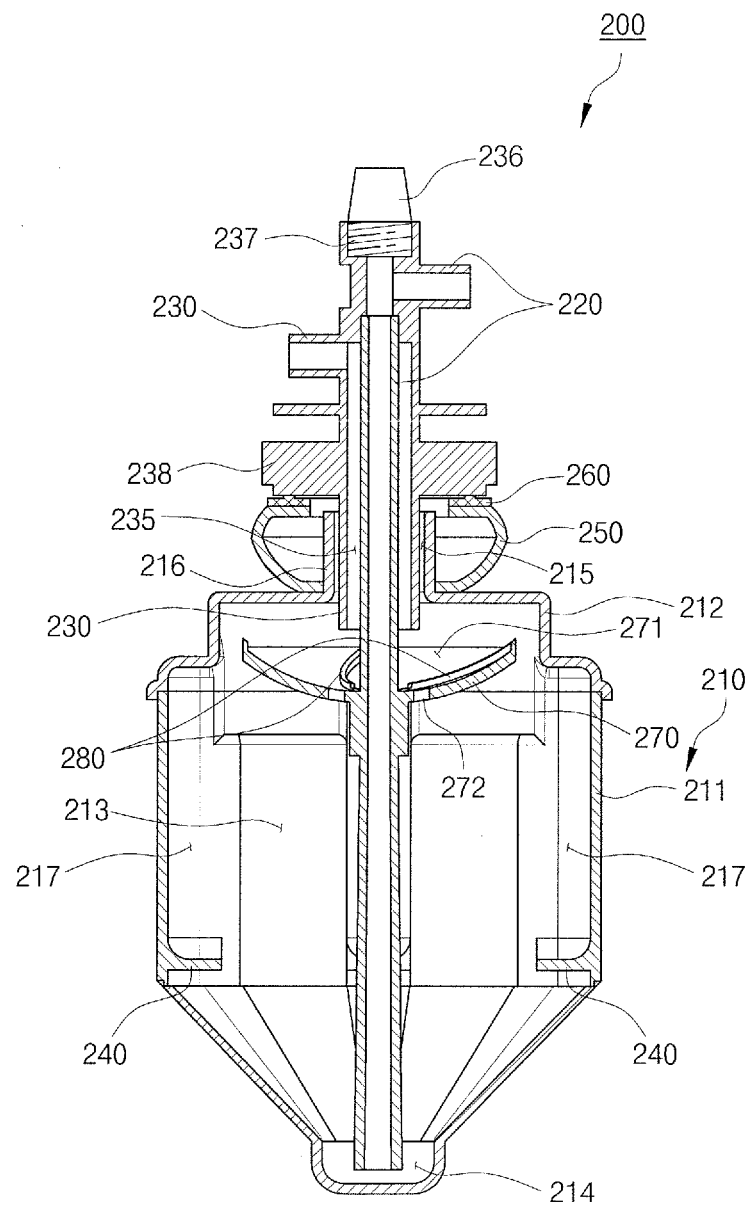
FIG. 5 is a schematic cross-sectional view of the regenerative cell extraction unit taken along the line V-V of FIG. 4.

FIG. 3 is a schematic, exploded perspective view of a regenerative cell extraction unit 200 according to an exemplary embodiment of the present invention. FIG. 4 is a schematic perspective view of the regenerative cell extraction unit 200 of FIG. 3 which has been assembled. FIG. 5 is a schematic cross-sectional view of the regenerative cell extraction unit 200 taken along the line V-V of FIG. 4.

Referring to FIGS. 1 and 3 through 5, the regenerative cell extraction unit 200 receives from the regenerative cell separation unit 100 a stem cell-containing aqueous solution obtained after the centrifugation of fat tissue by the regenerative cell separation unit 100 and extracts stem cells from the aqueous solution. When the regenerative cell extraction unit 200 is used alone without the regenerative cell separation unit 100, it may extract the stem cells directly from the fat tissue.

The regenerative cell extraction unit 200 performing the above function includes a main container 210, a first discharge pipe 220, and a second discharge pipe 230.

The main container 210 includes a body 211 and a main container cap 212. A housing portion 213 is formed inside the main container 210 to house a substance that is to be separated, such as fat tissue or an aqueous solution containing stem cells. A lower part of the body 211 may be gradually reduced in diameter toward a bottommost part of the body 211 or may remain unchanged. In particular, a concave groove 214 is formed in a bottommost part of the housing portion 213.

A through hole 215 is formed in a center of an upper surface of the main container cap 212 and penetrates from the upper surface of the main container cap 212 to a lower surface of the main container cap 212. Furthermore, a ring-shaped wall 216 protrudes upward from an outer circumference of the through hole 215.

Convex, protruding housing portions 217 are formed on an outer side of the main container 210. That is, the protruding housing portions 217 bulge outwards along a radius direction with respect to a central axis of rotation of the main container 210 and extend long along a heightwise direction of the main container 210.

In order to not affect the rotation of the main container 210, the protruding housing portions 217 are arranged symmetrical to the main container 210. In the current exemplary embodiment, four protruding housing portions 217 are arranged at intervals of 90 degrees with respect to the central axis of rotation c of the main container 210.

When the main container 210 rotates, a substance therein is separated into components according to weight. Here, heavy components of the substance are placed on the outer side of the main container 210, and light components are placed on an inner side of the main container 210. Since the protruding housing portions 217 are located farthest from the central of axis of rotation c of the main container 210, heaviest components of the substance are housed in the protruding housing portions 217. Stem cells separated from fat tissue are heavier than other components and thus are placed in the protruding housing portions 217 after centrifugation. This will be described in further detail later.

A lower end portion of each of the protruding housing portions 217 is blocked by a blocking member 240. That is, stem cells must be housed in the protruding housing portions 217 as a result of centrifugation. However, if the lower end portions of the protruding housing portions 217 are connected to a lower part of the main container 210, when the main container 210 rotates, a substance in the lower part of the main container 210 may move upward to the protruding housing portions 217 before it is properly centrifuged. Particularly, an aqueous solution may gush up, sweeping away stem cells already attached to the protruding housing portions 217. This is why the blocking member 240 is installed. The blocking member 240 enables stem cells already attached to the protruding housing portions 217 to be stably housed in the protruding housing portions 217, thereby preventing the stem cells from being lost.

Both the first discharge pipe 220 and the second discharge pipe 230 connect the housing portion 213 of the main container 210 to the outside of the main container 210. The first discharge pipe 220 and the second discharge pipe 230 form independent passages. The first discharge pipe 220 and the second discharge pipe 230 are coaxial with the main container 210. The first discharge pipe 220 is long and has a lower end portion disposed in the lower end portion of the main container 210, more accurately, in the groove 214. The second discharge pipe 230 is short and has a lower end portion disposed in an upper end portion of the main container 210.

Different substances may flow through the first discharge pipe 220 and the second discharge pipe 230 according to the uses of the first and second discharge pipes 220 and 230. In the current exemplary embodiment, a stem cell-containing aqueous solution obtained from the regenerative cell separation unit 100, a washing solution, etc. may be injected into the main container 210 through the first discharge pipe 220, and extracted stem cells, a washing solution, etc. may be discharged from the main container 210 through the first discharge pipe 220. On the other hand, air may flow into or out of the main container 210 through the second discharge pipe 230, and a used washing solution may be discharged through the second discharge pipe 230.

The specific configurations of the first and second discharge pipes 220 and 230 are completely identical to those of the main and auxiliary pipes 130 and 140 of the regenerative cell separation unit 100. That is, the first discharge pipe 220 is identical to the main pipe 130 of the regenerative cell separation unit 100, and the second discharge pipe 230 is identical to the auxiliary pipe 140.

The first discharge pipe 220 and the second discharge pipe 230 can be formed as separate pipes. In the current exemplary embodiment, however, the first discharge pipe 220 and the second discharge pipe 230 are integrated. That is, the first discharge pipe 220 is long, extends vertically, and has a bent upper part. The second discharge pipe 230 has a greater diameter than the first discharge pipe 220 and surrounds the first discharge pipe 220. An upper part of the second discharge pipe 230 is bent in a direction opposite to the direction in which the first discharge pipe 220 is bent. The inside of the second discharge pipe 230, more accurately, the space between an inner circumferential surface of the second discharge pipe 230 and an outer circumferential surface of the first discharge pipe 220 forms a fluid passage 235 through which air and fluids such as a washing solution can flow.

An insertion hole 237 is formed in an upper end of the first discharge pipe 220, and a cap 236 is coupled to the insertion hole 237 by screws. When the cap 236 is removed, an auxiliary discharge pipe (not shown) is inserted into the first discharge pipe 220 through the insertion hole 237, up to the groove 214 of the main container 210. The auxiliary discharge pipe is connected to a syringe to suck liquid substances placed in the groove 214 of the main container 210. Here, a needle connected to the syringe is used as the auxiliary discharge pipe. When the auxiliary discharge pipe is not in use, the insertion hole 237 is closed with the cap 236 to prevent the contamination of the housing portion 213 inside the main container 210.

The main container 210 should be rotated relative to the first discharge pipe 220 and the second discharge pipe 230, and the housing portion 213 of the main container 210 should be sealed by closing a gap between the first and second discharge pipes 220 and 230 and the main container 210.

In the current exemplary embodiment, a medium member 250 and a contact member 260 are employed to facilitate the rotation of the main container 210 and seal the housing portion 213 of the main container 210. That is, the medium member 250 employed in the current exemplary embodiment is ring-shaped, is fitted to the wall 216 of the main container cap 212, and is interposed between a flange 238, which is formed on an outer circumferential surface of the second discharge pipe 230, and the main container cap 212. The medium member 250 is made of a rubber material that can be elastically compressed. When compressed between the flange 238 of the second discharge pipe 230 and the main container cap 212, the medium member 250 can completely seal a gap between the protruding wall 216 (also the through hole 215) and the second discharge pipe 230.

However, when the medium member 250 rotates in accordance with the rotation of the main container 210, friction is created between the medium member 250 and the flange 238 because the medium member 250 made of a rubber material has a high coefficient of friction. The friction between the medium member 250 and the flange 238 impedes smooth rotation of the medium member 250 and produces high frictional heat. For this reason, the contact member 260 made of a material with a low coefficient of friction and a high coefficient of heat transfer is attached onto the medium member 250. In the current exemplary embodiment, the contact member 260, which is made of a ceramic material and is ring-shaped, is attached onto the medium member 250. The contact member 260 is closely attached to the flange 238 of the second discharge pipe 230 and makes a surface contact with the flange 238.

In the current exemplary embodiment, the first discharge pipe 220 and the second discharge pipe 230 are formed as a single body such that the second discharge pipe 230 surrounds the first discharge pipe 220. This structure brings about the need to seal a gap between the outer circumferential surface of the second discharge pipe 230 and the protruding wall 216. In other embodiments, however, the second discharge pipe 230 may be separate from the first discharge pipe 220 or may be omitted. In embodiments in which the second discharge pipe 230 is omitted, the first discharge pipe 220 is also inserted into the through hole 115. Thus, to facilitate the rotation of the main container 210 relative to the first discharge pipe 220 and close the gap between the first discharge pipe 220 and the wall 216, a flange (not shown) is formed on the outer circumferential surface of the first discharge pipe 220, and the medium member 250 and the contact member 260 are installed between the main container cap 212 and the flange (not shown) formed on the outer circumferential surface of the first discharge pipe 220.

The current exemplary embodiment provides a structure that allows substances (such as a washing solution) other than stem cells to be discharged from the regenerative cell extraction unit 200 through the second discharge pipe 230 while the main container 210 is rotating for centrifugation. That is, in the current exemplary embodiment, the rotation of the main container 210 may be stopped to discharge substances such as a washing solution from the lower part of the main container 210 through the first discharge pipe 220. However, even while the main container 210 is rotating, substances such as a washing solution can be discharged from the main container 210 by using a collection member 270 and guide members 280.

The collection member 270 is fitted to the first discharge pipe 220 and includes a concave collector portion 271 which temporarily accommodates a substance guided by the guide members 280 which will be described later. In the current exemplary embodiment, the collection member 270 is shaped like a concave discus. The collection member 270 is installed in an upper part of the main container 210, more accurately, close to the lower end portion of the second discharge pipe 230. In addition, a diameter of the collection member 270 is set such that an outer circumferential surface of the collection member 270 is close to an inner circumferential surface of the main container 210.

The guide members 280 are disposed on the collection member 270 and guide centrifugally separated substances, which are being rotated inside the main container 210, to the collector portion 271 of the collection member 270. In the current exemplary embodiment, four guide members 280 protrude upward from an upper surface of the collection member 270 and are arranged symmetrical to each other at intervals of 90 degrees. Additionally, the guide members 280 curve from the outer circumferential surface of the collection member 270 toward a center of the collection member 270. Accordingly, the guide members 280 are arranged on the collection member 270 in a whirlwind pattern.

The guide members 280 may not necessarily be curved but may be linear. The guide members 280 may be formed not all along a radius of the collection member 270. Instead, each of the guide members 280 may consist of short pieces formed on portions of the collection member 270 which contact substances. That is, the guide members 280 may have various shapes. Also, the number of the guide members 280 may be one or more.

Figure 9:
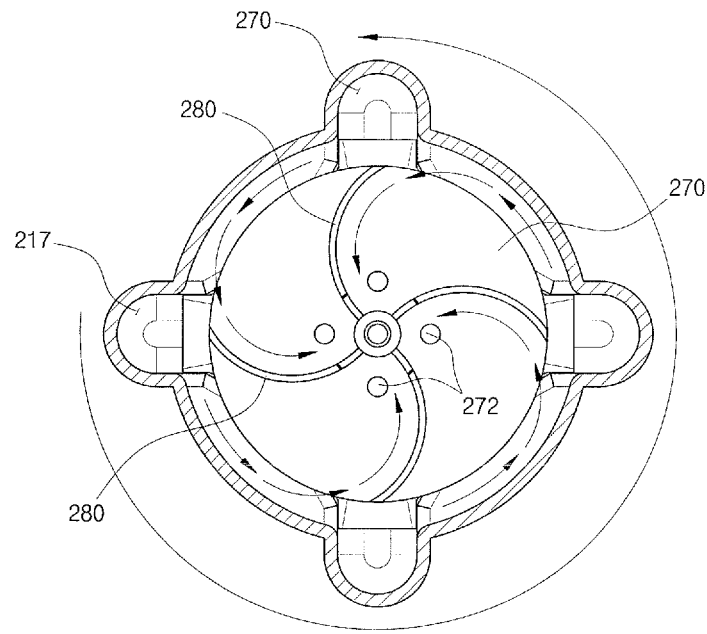
FIG. 9 is a diagram illustrating the process of collecting and discharging a substance using the collection member and guide members.

As the main container 210 rotates, a substance to be separated in the main container 210 also rotates while being pushed outwards by a centrifugal force. Accordingly, as described above, heavy components such as stem cells are housed in the protruding housing portions 217, while light components such as a washing solution are kept closely attached to the inner circumferential surface of the main container 210. When the main container 210 starts to rotate, the substance also rotates while rising toward a top of the main container 210. The substance rising above the collection member 270 comes into contact with and is interfered by the guide members 280. Accordingly, the substance is guided toward the center of the collection member 270 along the guide members 280, as shown in FIG. 9. Here, if a suction force is applied to the second discharge pipe 230 by a pump, the substance guided to the center of the collection member 270 is discharged to the outside through the second discharge pipe 230 by this suction force.

A plurality of holes 272 are formed in the center of the collection member 270. The holes 272 reduce pressure applied to the collection member 270 and, when a large amount of substance is rapidly introduced into the collection member 270, prevent the substance from overflowing.

The regenerative cell extraction unit 200 according to the current exemplary embodiment includes suction devices. In the current exemplary embodiment, the suction devices are a first pump 291 and a second pump 292. The first pump 291 is connected to the first discharge pipe 220 by a connection tube, and the second pump 292 is connected to the second discharge pipe 230 by another connection tube t4. Accordingly, fluids can be injected and discharged through the first and second discharge pipes 220 and 230.

In the current exemplary embodiment, since fluids should be injected and discharged through the first discharge pipe 220 and the second discharge pipe 230, a peristaltic pump that provides a suction force in both directions is used.

Referring to FIG. 1, a connection tube t1 connected to the main pipe 130 of the regenerative cell separation unit 100 has a photosensor 181. The photosensor 181 senses the color of a fluid flowing through the connection tube t1. In particular, when yellow fat cells or tissue is discharged from the regenerative cell separation unit 100 through the main pipe 130, the photosensor 181 senses the yellow color and transmits a signal indicating that the fat cells or tissue is being discharged to a controller (not shown) which will be described later.

Figure 10:
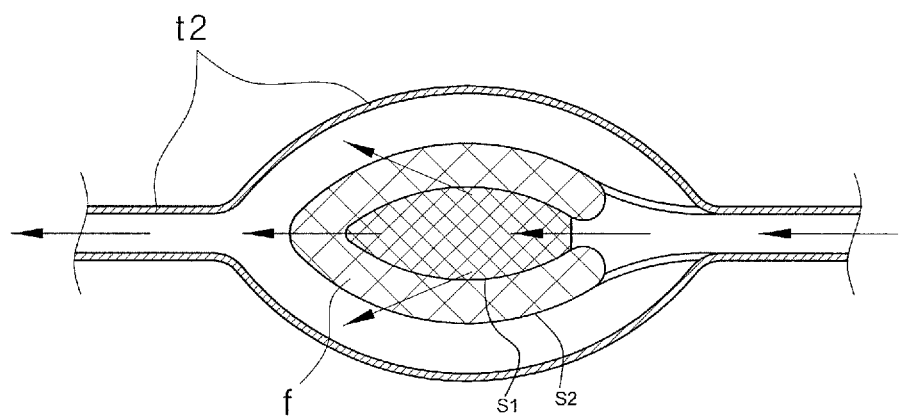
FIG. 10 is an enlarged view of a multi-filter shown in FIG. 1.

A connection tube t2 connected to the main pipe 130 of the regenerative cell separation unit 100 includes a multi-filter f that can filter out large tissue such as collagen mass. Referring to FIG. 10, the multi-filter f consists of two netted bags that overlap each other. Here, a small bag s1 is contained in a big bag s2. Since an aperture o is formed in a side of the multi-filter f, liquids or substances having small particles can pass through the multi-filter f, but large tissue such as collagen is trapped in the multi-filter f.

Further, a connection tube t3 connected to the first discharge pipe 220 of the regenerative cell extraction unit 200 and a connection tube t4 connected to the second discharge pipe 230 respectively include sensors 293 and 294 which sense air flowing through the connection tubes t3 and t4. Particularly, the connection tubes t3 and t4 sense air released from the regenerative cell extraction unit 200 through the first and second discharge pipes 220 and 230 and transmit signals indicating the release of the air to the controller.

The regenerative cell extraction system 300 according to the current exemplary embodiment includes the controller (not shown) which controls the operations of elements including the regenerative cell separation unit 100, the regenerative cell extraction unit 200, the rotating jig (not shown), and various valves. All operations are controlled by the controller.

Hereinafter, a process in which the regenerative cell extraction system 300 including the above elements separates fat tissue will be described with reference to the accompanying drawings.

Figure 6:
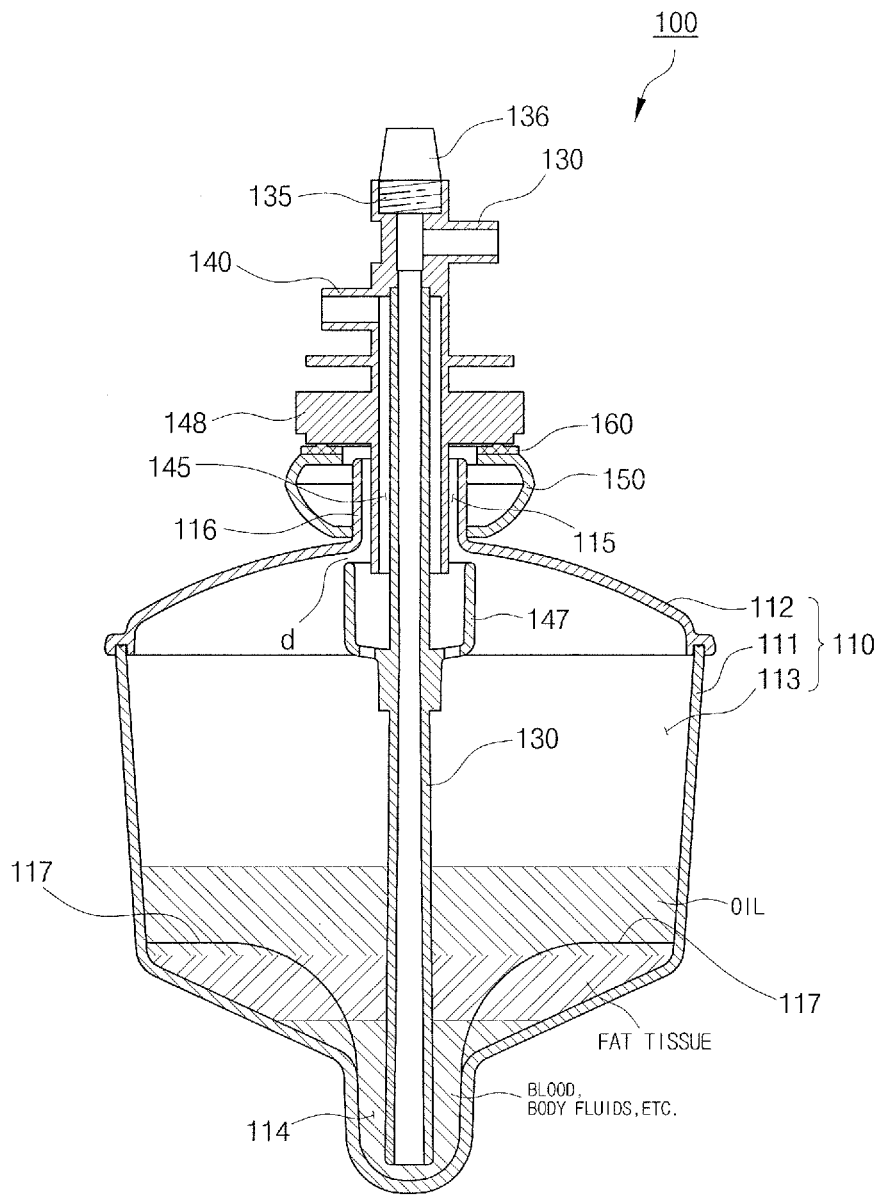
FIG. 6 is a diagram illustrating fat tissue gravitationally separated from substance form human body after being washed in the regenerative cell separation unit.
Figure 7:
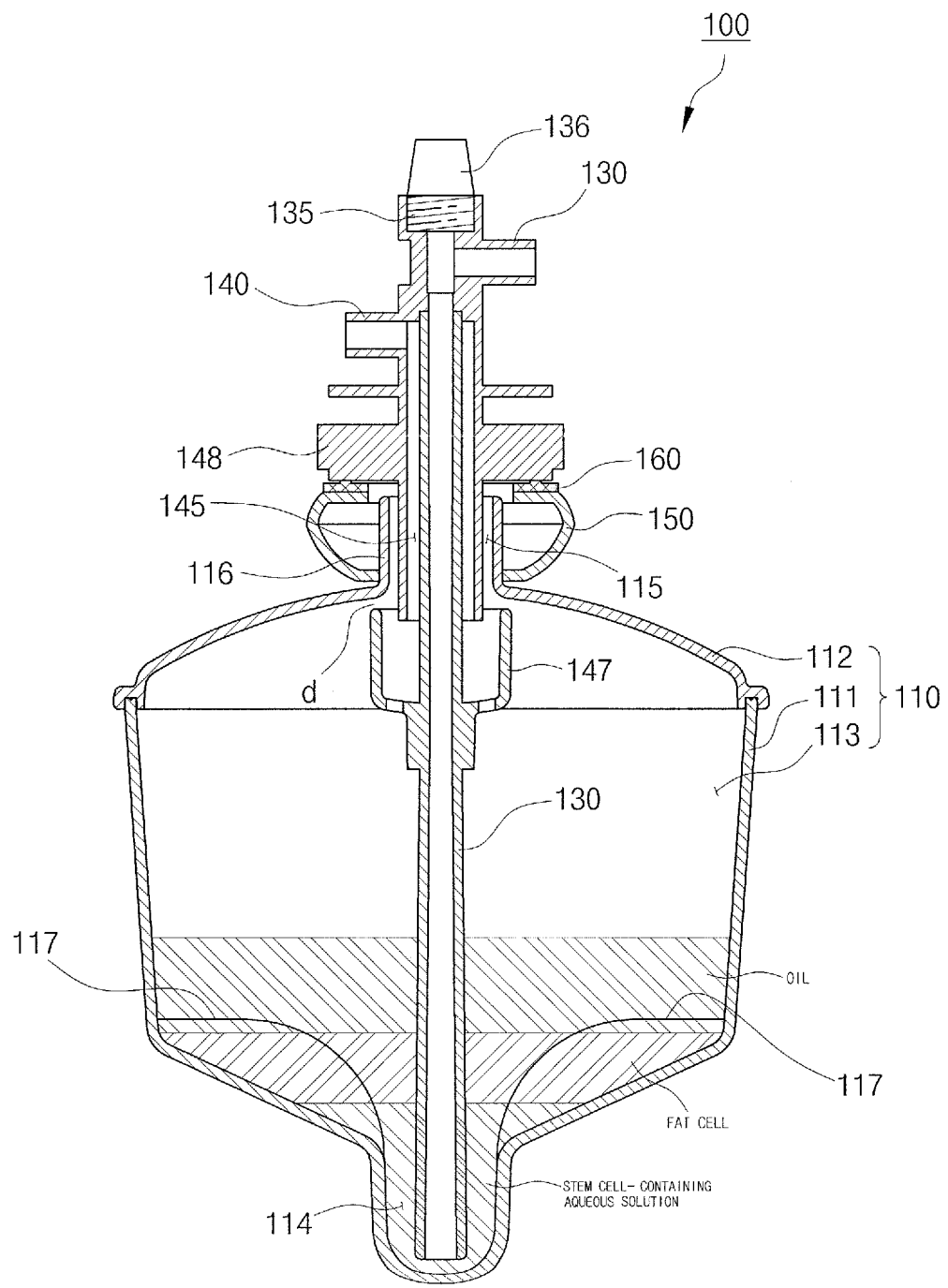
FIG. 7 is a diagram illustrating the result of centrifuging the fat tissue after introducing an enzyme into the regenerative cell separation unit.
Figure 8:
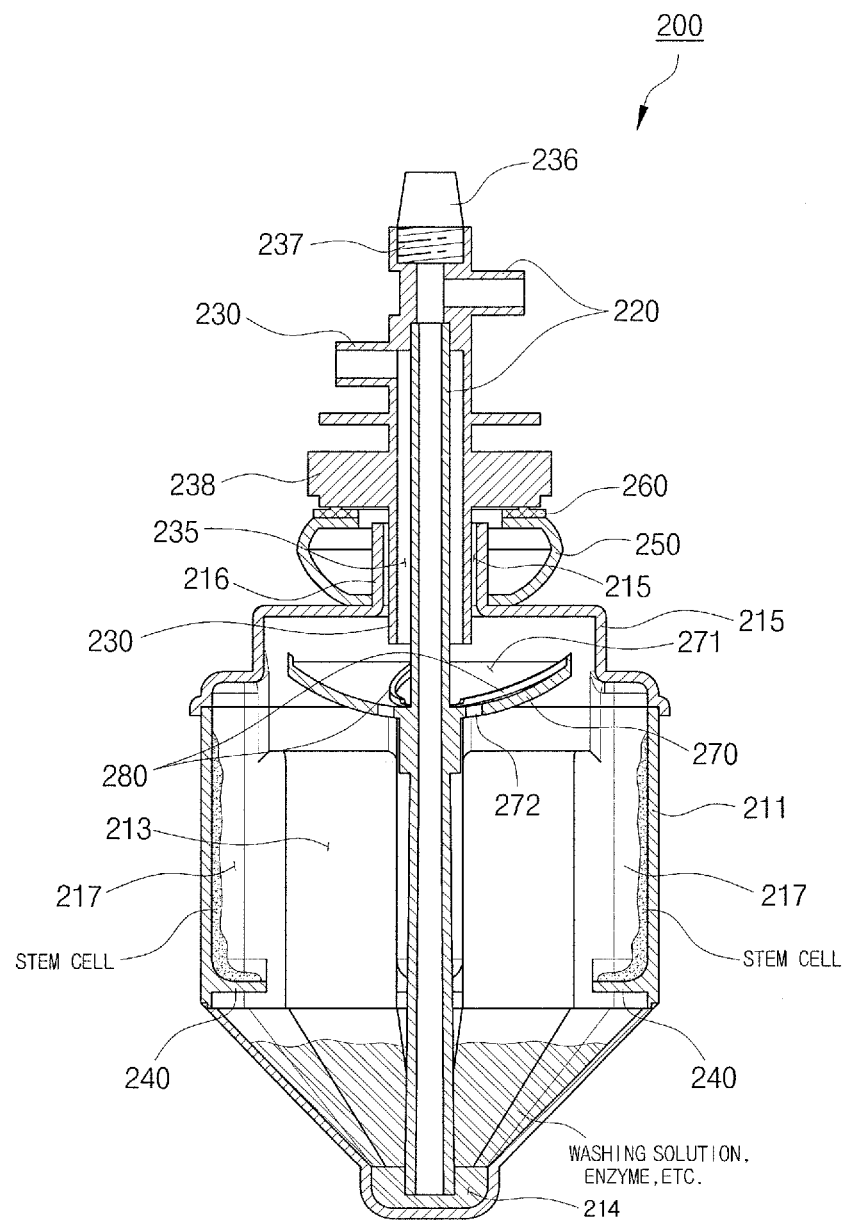
FIG. 8 is a diagram illustrating the result of centrifuging a stem cell-containing aqueous solution in the regenerative cell extraction unit without using a collection member.

FIG. 6 is a diagram illustrating fat tissue separated from substance form human body after being washed in the regenerative cell separation unit 100. FIG. 7 is a diagram illustrating the result of centrifuging the fat tissue after introducing an enzyme into the regenerative cell separation unit 100. FIG. 8 is a diagram illustrating the result of centrifuging a stem cell-containing solution in the regenerative cell extraction unit 200 without using the collection member 270.

Referring to FIG. 1, the regenerative cell separation unit 100 and the regenerative cell extraction unit 200 are connected to each other by a plurality of connection tubes t1, t2, and t, and the connection tubes t1, t2 and t are connected to various bags including a bag b1 that stores a washing solution, a bag b2 that stores enzymes, a bag b3 that stores washed fat tissue, a bag b4 that stores waste liquids, and a bag b5 that stores stem cells. Additionally, the connection tubes t1, t2 and t may be connected to various other bags including a bag (not shown) that stores fat cells and a bag that stores extracted stem cells in a frozen state.

First, fat tissue that is to be separated is put into the regenerative cell separation unit 100 through the main pipe 130. For example, the fat tissue may be extracted from the human body using a syringe, and then the extracted fat tissue may be put into the regenerative cell separation unit 100. To prevent contamination of the fat tissue while being transferred to the regenerative cell separation unit 100, a syringe needle may be inserted into the human body, and a tube connected to the syringe may be connected to the main pipe 130. Then, a negative pressure atmosphere may be created inside the sub container 110 by using the pump 170. Accordingly, the fat tissue may be injected into the sub container 110 directly from the human body.

Once the fat tissue is introduced into the sub container 110 as described above, a washing solution is transferred to the regenerative cell separation unit 100 by opening a valve v2 and operating the pump 170. Then, the regenerative cell separation unit 100 is repeatedly rotated and stopped by operating the rotating jig. As the rotation and stoppage of the regenerative cell separation unit 100 are repeated at regular intervals, the fat tissue and the washing solution are mixed and centrifuged. Accordingly, the fat tissue with blood-derived contaminants is washed.

The sub container 110 is stopped and left for approximately one minute. Then, as shown in FIG. 6, heavy components such as the washing solution, blood, and body fluids are placed on the bottom of the sub container 100, the washed fat tissue is placed on the heavy components, and oil components are placed on the washed fat tissue.

Next, the pump 170 is operated again to discharge the blood, the washing solution, etc. on the bottom of the sub container 110 through the main pipe 130. After the washing solution and the like are all discharged, the yellow fat tissue is discharged through the main pipe 130. Here, the photosensor 181 of the connection tube a senses the yellow color of the fat tissue and transmits a signal indicating the discharge of the fat tissue to the controller. Accordingly, the controller stops the operation of the pump 170 and repeats the above process three or four times until the fat tissue is completely washed.

After the blood-derived contaminants, the body fluids and the oil components are separated from the fat tissue extracted from the human body and then the fat tissue is completed washed as described above, a portion of the washed fat tissue may be transferred to and stored in the bag b3, when necessary.

Next, collagenase is transferred from the enzyme bag b2 to the regenerative cell separation unit 100 by operating the pump 170 and opening a valve v3. When the collagenase is put into the sub container 110, the operation of the pump 170 is stopped, and the sub container 110 is rotated for approximately 30 minutes to mix the collagenase and the washed fat tissue. Here, the temperature of the sub container 110 is maintained at approximately 37° C. by using a rotating device such as the rotating jig. The collagenase breaks down the fat tissue into components, and the components of the fat tissue are centrifuged by the rotation of the sub container 110. Then, the rotating sub container 110 is stopped and left for approximately one minute. Accordingly, an aqueous solution that contains stem cells derived from the fat tissue is placed on the bottom of the sub container 110 since it is a relatively heavy component, and matured fat cells and oil components are placed on the aqueous solution, as shown in FIG. 7.

Next, the stem cell-containing aqueous solution is transferred to the regenerative cell extraction unit 200 through the main pipe 130 by operating the pump 170 again. While the stem cell-containing aqueous solution is being transferred to the regenerative cell extraction unit 200, the pump 170 and the second pump 292 are operated together. If the photosensor 181 senses the yellow color again, it indicates that the fat cells are being discharged after the discharge of the stem cell-containing aqueous solution is completed. Thus, the operations of the pumps 170 and 292 are stopped. When necessary, the matured fat cells may be stored in a separate bag.

After the stem cell-containing aqueous solution is all put into the main container 210 of the regenerative cell extraction unit 200 as described above, the process of extracting the stem cells is performed by optionally using the collection member 270 and the guide members 280.

When the collection member 270 and the guide members 280 are not used, all valves are closed, and the operations of the pumps are stopped. In this state, the main container 210 is rotated for approximately five minutes and then decelerated naturally. In this process, the stem cell-containing aqueous solution is centrifuged. As a result, as shown in FIG. 8, relatively heavy stem cells are pressed and attached to inner surfaces of walls of the protruding housing portions 217 by a centrifugal force, and body fluids, a washing solution, an enzyme, etc. are placed in the lower part of the main container 210. One important thing to remember here is to naturally decelerate the main container 210 when stopping the rotation of the main container 210. This is because if a brake is artificially applied to the rotating main container 210, the stem cells attached to the inner surfaces of the walls of the protruding housing portions 217 may fall down to the bottom of the main container 210.

After centrifugation, the first pump 291 is operated to transfer aqueous solutions such as body fluids to the waste liquid bag b4 through the first discharge pipe 220. If the sensor 293 of the connection tube t3 connected to the first discharge pipe 220 senses air, it indicates that all of the aqueous solutions have been discharged. Accordingly, the operation of the first pump 291 is stopped, and a next operation is performed.

When the collection member 270 and the guide members 280 are used, the second pump 292 is operated along with the rotation of the main container 210, thereby providing a suction force through the second discharge pipe 230. As the main container 210 rotates, the stem cell-containing aqueous solution also rotates. Accordingly, the stem cells are attached to the inner surfaces of the walls of the protruding housing portions 217, and the remaining aqueous solution moves upward while being rotated continuously. When rising above the collection member 270, the rotating aqueous solution is interfered by the guide members 280 and thus is guided toward the center of the collection member 270 along the guide members 280, as shown in FIG. 9.

Since the second discharge pipe 230 is disposed above the center of the collection member 270, the aqueous solution is discharged to the outside through the fluid passage 235 between the first discharge pipe 220 and the second discharge pipe 230 by the suction force of the second pump 292 and is transferred to the waste liquid bag b4. Here, if the sensor 294 of the connection tube t4 connected to the second discharge pipe 230 senses air, it indicates that the aqueous solution has all been discharged. Accordingly, the operation of the second pump 292 is stopped. Then, the main container 210 is naturally decelerated to a halt. As a result, only the stem cells remain attached to the inner surfaces of the walls of the protruding housing portions 217 inside the main container 210. Any portion of the aqueous solution, which remains in the lower part of the main container 210, is transferred to the waste liquid bag b4 through the first discharge pipe 220 by operating the first pump 291.

After the stem cell-containing aqueous solution is centrifuged as described above, a very small amount of washing solution is injected into the main container 210 to wash the stem cells attached to the inner surfaces of the walls of the protruding housing portions 217, and the rotation and stoppage of the main container 210 are repeated approximately five times. Then, the main container 210 is rotated again and decelerated naturally. If the main container 210 is accelerated and decelerated by repeating the rotation and stoppage of the main container 210 as described above, the stem cells attached to the inner surfaces of the walls of the protruding housing portions 217 fall down to the bottom of the main container 210. Thus, stem cells finally obtained by repeating the above stem cell extraction process several times contain a minimum amount of foreign substance.

Finally, the stem cells existing in the lower part of the main container 210 are transferred to the stem cell bag b5 through the first discharge pipe 220. In so doing, the stem cell extraction process is completed.

Since all of the above-described processes are automatically performed by the regenerative cell extraction system 300, they can be performed with precision and efficiency. Furthermore, the regenerative cell extraction system 300 is kept sealed, eliminating the risk of contamination.

Most of all, since the regenerative cell separation unit 100 produces stem cell-containing concentrate through centrifugation and the regenerative cell extraction unit 200 centrifuges the stem cell-containing concentrate, the process of extracting stem cells can be performed efficiently, and extraction yields can be increased.

Figure 11:
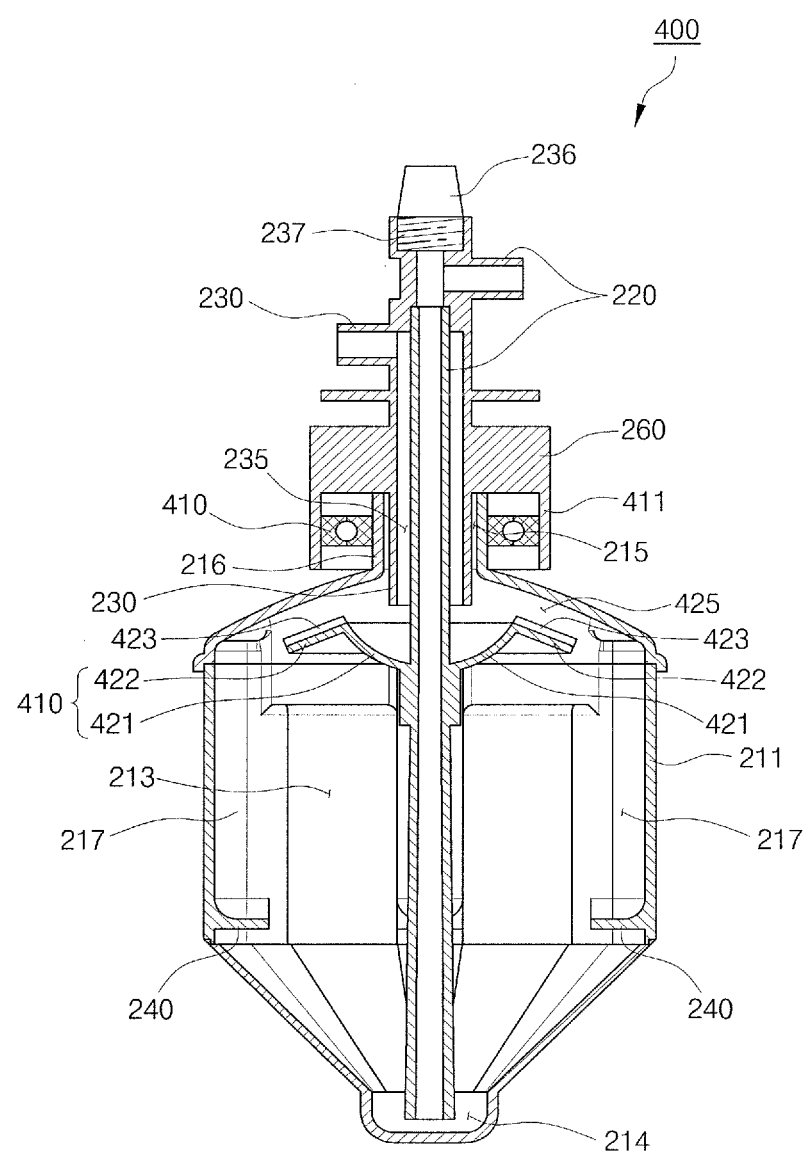
FIG. 11 is a diagram illustrating a regenerative cell extraction unit according to another exemplary embodiment of the present invention.

FIG. 11 is a diagram illustrating a regenerative cell extraction unit 400 according to another exemplary embodiment of the present invention.

Referring to FIG. 11, the regenerative cell extraction unit 400 according to the current exemplary embodiment is substantially the same as the regenerative cell extraction unit 300 according to the previous exemplary embodiment. However, they are different in that the regenerative cell extraction unit 400 according to the current exemplary embodiment employs a bearing 410 as a medium member and that the shape of a collection member 420 is different from that of the collection member 270 according to the previous exemplary embodiment. For simplicity, a description of elements substantially identical to those of the previous embodiment described above will be omitted, and differences between the current and previous embodiments will mainly be described.

In the current exemplary embodiment, a cover 411 having an aperture in a lower part thereof is disposed on an outer circumferential surface of a second discharge pipe 230, and the bearing 410 is supported between an inner circumferential surface of the cover 411 and the outer circumferential surface of the second discharge pipe 230. Thus, a main container 210 is rotatable relative to a first discharge pipe 220 and the second discharge pipe 230. In addition, since the bearing 410 used herein has a sealing function, it can seal a gap between the second discharge pipe 230 and a wall 216.

The collection member 420 includes a discus-shaped body 421 fitted and coupled to the first discharge pipe 220. In addition, an inclined portion 422 slopes downward from an outer circumferential surface of the body 421 to face a main container cap 212. As in the previous embodiment, guide members 423 protrude upward from an upper surface of the inclined portion 422.

Since the inclined portion 422 is placed very close to the main container cap 212, a gap between the inclined portion 422 and the main container cap 212 may serve as a fluid passage 425. That is, in the current exemplary embodiment, liquids moving upward along an inner surface of the main container 210 while being rotated are collected in the discus-shaped body 421 through the fluid passage 425 and are then discharged through the second discharge pipe 230.

Valves v1 through v9 are installed in connection tubes. In the current exemplary embodiment, solenoid valves are used.

A regenerative cell extraction unit and system according to the present invention has been described and illustrated in the drawings as separating fat tissue. However, the regenerative cell extraction unit and system according to the present invention can also pulverize and then separate other tissues and extract stem cells from these tissues.

A regenerative cell separation unit of a regenerative cell extraction system according to the present invention produces a stem cell-containing aqueous solution by stirring, washing, breaking down and centrifuging tissue. Then, a regenerative cell extraction unit of the regenerative cell extraction system centrifuges the stem cell-containing aqueous solution. Thus, the process of extracting stem cells can be performed efficiently, and stem cell extraction yields can be increased.

In addition, all processes from extracting fat tissue from the human body to extracting stem cells from the fat tissue are automatically performed by the regenerative cell extraction system. Therefore, the processes can be performed with increased efficiency and controlled with precision.

Furthermore, since the regenerative cell extraction system is kept sealed, the contamination of fat tissue or cells can be prevented during the process of extracting stem cells from the fat tissue or washing the fat tissue.

While this invention has been particularly shown and described with reference to exemplary embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims and their equivalents.

What is claimed is:

1. A regenerative cell extraction unit comprising:
   a main container which is rotated by a torque applied from an external source and comprises a housing portion accommodating a substance that is to be separated;
   a hollow first discharge pipe which is inserted into the main container such that an end portion of the first discharge pipe is disposed in a lower part of the main container and that the other end portion of the first discharge pipe is disposed outside the main container;
   a suction device which is connected to the first discharge pipe so as to suck and discharge components, which are placed in a lower end portion of the main container after being centrifuged by the rotation of the main container, from the main container through the first discharge pipe;
   a collection member which is disposed in the housing portion of the main container and comprises a concave collector portion;
   a plurality of guide members which are formed on the collection member, are positioned to interfere with centrifuged components which are pressed toward an inner surface of a wall of the main container, and guide rotating components to the concave collector portion of the collection member;
   a hollow second discharge pipe which is inserted into the main container, has an end portion disposed above the collector portion of the collection member, and has the other end portion disposed outside the main container; and
   a second pump which is connected to the second discharge pipe, provides a suction force to the second discharge pipe, and discharges the components collected on the collection member to the outside through the second discharge pipe.

2. The regenerative cell extraction unit of claim 1, further comprising a plurality of protruding housing portions which bulge outwards along a radius direction with respect to a center of rotation of the main container to accommodate relatively heavy components among components centrifuged from the substance and are arranged at intervals of a predetermined angle along a circumferential direction of the housing portion, wherein each of the protruding accommodation portions extends along a direction perpendicular to a radius direction with respect to a center of rotation of the main container and is tube-shaped.

3. The regenerative cell extraction unit of claim 1, wherein a lower part of the housing portion narrows toward a lower end of the housing portion.

4. The regenerative cell extraction unit of claim 1, wherein a concave groove facing an interior of the housing portion and which is formed in the lower end of the housing portion.

5. The regenerative cell extraction unit of claim 1, wherein the suction device connected to the first discharge pipe is a first pump and further comprising a hollow auxiliary discharge pipe which is inserted into the first discharge pipe, has an end portion disposed in the lower end portion of the main container, and has the other end portion connected to a syringe outside the main container, wherein the components placed in the lower end portion of the main container are sucked to the first discharge pipe by the first pump and are discharged through the first discharge pipe or are sucked to the auxiliary discharge pipe by the syringe and are discharged through the auxiliary discharge pipe.

6. A regenerative cell extraction unit comprising:
   a main container which is rotated by a torque applied from an external source and comprises a housing portion accommodating a substance that is to be separated;
   a hollow first discharge pipe which is inserted into the main container such that an end portion of the first discharge pipe is disposed in a lower part of the main container and that the other end portion of the first discharge pipe is disposed outside the main container;
   a suction device which is connected to the first discharge pipe so as to suck and discharge components, which are placed in a lower end portion of the main container after being centrifuged by the rotation of the main container, from the main container through the first discharge pipe;
   a plurality of protruding housing portions which bulge outwards along a radius direction with respect to a center of rotation of the main container to accommodate relatively heavy components among components centrifuged from the substance and are arranged at intervals of a predetermined angle along a circumferential direction of the housing portion;
   a collection member which is disposed in the housing portion of the main container and comprises a concave collector portion;
   a plurality of guide members which are formed on the collection member, are positioned to interfere with centrifuged components which are pressed toward an inner surface of a wall of the main container, and guide rotating components to the concave collector portion of the collection member;
   a hollow second discharge pipe which is inserted into the main container, has an end portion disposed above the collector portion of the collection member, and has the other end portion disposed outside the main container; and
   a second pump which is connected to the second discharge pipe, provides a suction force to the second discharge pipe, and discharges the components collected on the collection member to the outside through the second discharge pipe.

7. The regenerative cell extraction unit of claim 6, wherein the collection member is shaped like a concave discus, and the guide members curve toward a center of the collection member from a circumference of the collection member and are arranged on an upper surface of the collection member at intervals of a predetermined angle.

8. The regenerative cell extraction unit of claim 6, wherein a plurality of holes are formed in the center of the collection member to penetrate from the upper surface of the collection member to a lower surface of the collection member.

9. The regenerative cell extraction unit of claim 6, wherein the second discharge pipe surrounds the first discharge pipe, and the components placed on the collector of the collection member are discharged through a fluid passage between the first discharge pipe and the second discharge pipe by the second pump.

10. The regenerative cell extraction unit of claim 9, wherein the second discharge pipe is fitted into a through hole formed in an upper part of the main container and further comprising a medium member which enables the main container to rotate relative to the second discharge pipe while sealing a gap between an outer circumferential surface of the second discharge pipe and an inner circumferential surface of the through hole of the upper part of the main container.

11. The regenerative cell extraction unit of claim 10, wherein a ring-shaped flange is formed along the outer circumferential surface of the second discharge pipe, the medium member is ring-shaped, is made of a rubber material which is compressible and elastic, and is compressed between a lower surface of the flange and an upper surface of the main container in a state where the second discharge pipe is inserted into the main container, and a ring-shaped contact member having a lower coefficient of friction than rubber is formed on an upper surface of the medium member and is attached closely to the flange, wherein while being compressed between the main container and the flange, the medium member and the contact member rotate in accordance with the rotation of the main container and seal the gap between the inner circumferential surface of the through hole formed in the upper part of the main container and the outer circumferential surface of the second discharge pipe.

12. The regenerative cell extraction unit of claim 6, wherein a connection tube is connected to the second discharge pipe and further comprising a sensor which is installed in the connection tube to sense whether air is discharged through the second discharge pipe.

13. The regenerative cell extraction unit of claim 1, wherein a connection tube is connected to the first discharge pipe and further comprising a sensor which is installed in the connection tube to sense whether air is discharged through the first discharge pipe.

14. The regenerative cell extraction unit of claim 1, wherein the first discharge pipe is fitted into a through hole formed in an upper part of the main container and further comprising a medium member which enables the main container to rotate relative to the first discharge pipe while sealing a gap between an outer circumferential surface of the first discharge pipe and an inner circumferential surface of the through hole.

15. The regenerative cell extraction unit of claim 14, wherein a ring-shaped flange is formed along the outer circumferential surface of the first discharge pipe, the medium member is ring-shaped, is made of a rubber material which is compressible and elastic, and is compressed between a lower surface of the flange and an upper surface of the main container in a state where the first discharge pipe is inserted into the main container, and a ring-shaped contact member having a lower coefficient of friction than rubber is formed on an upper surface of the medium member and is attached closely to the flange, wherein while being compressed between the main container and the flange, the medium member and the contact member rotate in accordance with the rotation of the main container and seal the gap between the inner circumferential surface of the through hole formed in the upper part of the main container and the outer circumferential surface of the first discharge pipe.

16. The regenerative cell extraction unit of claim 2, wherein a blocking member is formed in a lower end portion of each of the protruding housing portions to block between the lower part of the housing portion of the main container and a corresponding one of the protruding housing portions.

17. A regenerative cell extraction system comprising:
a regenerative cell separation unit which separates tissue; and
a regenerative cell extraction unit that comprises:
a main container which is rotated by a torque applied from an external source and comprises a housing portion accommodating a substance that is to be separated;
a hollow first discharge pipe which is inserted into the main container such that an end portion of the first discharge pipe is disposed in a lower part of the main container and that the other end portion of the first discharge pipe is disposed outside the main container;
a suction device which is connected to the first discharge pipe so as to suck and discharge components, which are placed in a lower end portion of the main container after being centrifuged by the rotation of the main container, from the main container through the first discharge pipe; and
a plurality of protruding housing portions which bulge outwards along a radius direction with respect to a center of rotation of the main container to accommodate relatively heavy components among components centrifuged from the substance and are arranged at intervals of a predetermined angle along a circumferential direction of the housing portion,
wherein the regenerative cell separation unit comprises:
a sub container which is rotated by a torque applied from an external source and comprises a space in which tissue is housed;
a hollow main pipe which is inserted into the sub container such that an end portion of the main pipe is disposed in a lower part of the sub container; and
a pump which is connected to the main pipe and provides a suction force to the main pipe, and wherein the regenerative cell extraction unit is separate from the regenerative cell separation unit, receives a regenerative cell-containing substance, which is obtained after the tissue is centrifuged by the regenerative cell separation unit, from the regenerative cell separation unit through the main pipe, and extracts regenerative cells from the substance by centrifuging the substance.

18. The regenerative cell extraction system of claim 17, wherein a plurality of stirring wings bulge from an inner surface of a wall of the sub container toward the space of the sub container so as to facilitate the centrifugation of the tissue.

19. The regenerative cell extraction system of claim 17, wherein auxiliary stirring wings protrude from an outer circumferential surface of the main pipe.

20. The regenerative cell extraction system of claim 17, wherein an auxiliary pipe, which is a passage independent from the main pipe, is inserted into the sub container to connect the space of the sub container to the outside of the sub container, the main pipe is connected to a plurality of storage bags and the first discharge pipe of the regenerative cell extraction unit by a plurality of connection tubes connected thereto, and the regenerative cell-containing substance discharged from the regenerative cell separation unit through the main pipe is transferred to the regenerative cell extraction unit through the first discharge pipe.

21. The regenerative cell extraction system of claim 17, wherein a connection tube which connects the main pipe of the regenerative cell separation unit to the first discharge pipe of the regenerative cell extraction unit comprises a multi-filter which filters out foreign substances.

22. The regenerative cell extraction system of claim 17, wherein a connection tube is connected to the main pipe, and a photosensor is installed in the connection tube to sense colors of the substances discharged from the regenerative cell separation unit.

23. The regenerative cell extraction system of claim 17, further comprising a rotating jig to which the main container and the sub container are fitted, wherein the rotating jig rotates the main container and the sub container at a constant rotational speed and heats the main container and the sub container to a constant temperature.

\* \* \* \* \*